United States Patent [19]
Lam

[11] Patent Number: 5,556,413
[45] Date of Patent: Sep. 17, 1996

[54] COILED STENT WITH LOCKING ENDS

[75] Inventor: Sharon Lam, San Jose, Calif.

[73] Assignee: Advanced Cardiovascular Systems, Inc., Santa Clara, Calif.

[21] Appl. No.: 209,827

[22] Filed: Mar. 11, 1994

[51] Int. Cl.$^6$ .................................................. A61M 29/00
[52] U.S. Cl. ................................ 606/198; 623/1; 623/12
[58] Field of Search ................................ 606/191, 198, 606/200, 108, 104, 105; 623/1, 12; 128/898

[56] References Cited

U.S. PATENT DOCUMENTS

| | | |
|---|---|---|
| 3,657,744 | 4/1972 | Ersek . |
| 4,512,338 | 4/1985 | Balko et al. . |
| 4,553,545 | 11/1985 | Maass et al. . |
| 4,560,374 | 12/1985 | Hammerslag . |
| 4,580,568 | 4/1986 | Gianturco . |
| 4,655,771 | 4/1987 | Wallsten . |
| 4,733,665 | 3/1988 | Palmaz . |
| 4,739,762 | 4/1988 | Palmaz . |
| 4,740,207 | 4/1988 | Kreamer . |
| 4,762,128 | 8/1988 | Rosenbluth . |
| 4,776,337 | 10/1988 | Palmaz . |
| 4,795,458 | 1/1989 | Regan . |
| 4,800,882 | 1/1989 | Gianturco . |
| 4,830,003 | 5/1989 | Wolff et al. . |
| 4,856,516 | 8/1989 | Hillstead . |
| 4,877,030 | 10/1989 | Beck et al. . |
| 4,878,906 | 11/1989 | Lindemann et al. . |
| 4,886,062 | 12/1989 | Wiktor . |
| 4,893,623 | 1/1990 | Rosenbluth . |
| 4,907,336 | 3/1990 | Gianturco . |
| 4,913,141 | 4/1990 | Hillstead . |
| 4,922,905 | 5/1990 | Strecker . |
| 4,950,227 | 8/1990 | Savin et al. . |
| 4,969,458 | 11/1990 | Wiktor . |
| 4,969,890 | 11/1990 | Sugita et al. . |
| 4,986,831 | 1/1991 | King et al. . |
| 4,994,071 | 2/1991 | MacGregor . |
| 4,998,539 | 3/1991 | Delsanti . |

(List continued on next page.)

FOREIGN PATENT DOCUMENTS

| | | |
|---|---|---|
| 0382014 | 8/1990 | European Pat. Off. .................. 623/1 |
| 0408245A1 | 1/1991 | European Pat. Off. . |
| 0541443 | 5/1993 | European Pat. Off. .................. 623/1 |
| 364045A1 | 6/1987 | Germany . |
| 2135585 | 9/1984 | United Kingdom . |
| WO98/08433 | 9/1989 | WIPO . |

OTHER PUBLICATIONS

Wright et al.: Percutaneous Endovascular Stents: An Experimental Evaluation, 69–72, 1985, *Radiology Journal.*

Dotter: Transluminal Expandable Nitinol Coil Stent Grafting: Preliminary Report, pp. 259–260, Apr. 1983, *Radiology Journal.*

Cragg et al.: Non–Surgical Placement of Arterial Endoprotheses: A New Technique Using Nitinol Wire, pp. 261–263, Apr. 1983, *Radiology Journal.*

Dotter, Charles T.: Transluminally Placed Coilspring Endarterial Tube Grafts, pp. 329–332,09–Oct. 1969, *Investigative Radiology.*

C. R. Bard: PE Plus Peripheral Balloon Dilatation Catheter, Aug. 1985, *CR Bard, Inc..*

Duprat et al.: Flexible Balloon–Expanded Stent for Small Vessels, pp. 276–278, 1987, *Radiology Journal.*

Maass et al.: Radiological Follow–up of Transluminally Inserted Vascular Endoprosthese: An Experimental Study Using Expanding Spirals, pp. 659–663, 1984, *Radiology Journal.*

Palmaz et al.: Expandable Intraluminal Graft: A Preliminary Study, pp. 73–77, 1985, *Radiology Journal.*

*Primary Examiner*—Gary Jackson
*Assistant Examiner*—William W. Lewis
*Attorney, Agent, or Firm*—Fulwider Patton Lee & Utecht

[57] ABSTRACT

An intravascular stent comprising a cylindrical body capable of expansion having end assemblies capable of locking in an expanded state. The end assemblies may have a series of tabs and apertures that interlock and rotate as the stent ends expand to an open position to support a section of vasculature or other body lumen. The stent is bio-compatible, may be bio-erodible, and capable of localized drug delivery.

27 Claims, 9 Drawing Sheets

U.S. PATENT DOCUMENTS

| | | |
|---|---|---|
| 5,002,560 | 3/1991 | Machold et al. . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Gianturco et al. . |
| 5,037,392 | 8/1991 | Hillstead . |
| 5,037,427 | 8/1991 | Harada et al. . |
| 5,059,211 | 10/1991 | Stack et al. . |
| 5,061,275 | 10/1991 | Wallsten et al. . |
| 5,062,829 | 11/1991 | Pryor et al. . |
| 5,064,435 | 11/1991 | Porter . |
| 5,078,726 | 1/1992 | Kreamer . |
| 5,078,736 | 1/1992 | Behl . |
| 5,084,065 | 1/1992 | Weldon et al. . |
| 5,092,877 | 3/1992 | Pinchuk . |
| 5,102,417 | 4/1992 | Palmaz .................................. 606/195 |
| 5,104,404 | 4/1992 | Wolff . |
| 5,108,416 | 4/1992 | Ryan et al. . |
| 5,116,318 | 5/1992 | Hillstead . |
| 5,116,365 | 5/1992 | Hillstead . |
| 5,122,154 | 9/1992 | Rhodes . |
| 5,123,917 | 6/1992 | Lee . |
| 5,133,732 | 7/1992 | Wiktor . |
| 5,135,536 | 8/1992 | Hillstead . |
| 5,161,547 | 11/1992 | Tower . |
| 5,163,958 | 11/1992 | Pinchuk . |
| 5,171,262 | 12/1992 | MacGregor . |
| 5,183,085 | 2/1993 | Timmermans . |
| 5,192,297 | 3/1993 | Hull . |
| 5,192,307 | 3/1993 | Wall . |
| 5,195,984 | 3/1993 | Schatz . |
| 5,197,978 | 3/1993 | Hess . |

COILED STENT WITH LOCKING ENDS

BACKGROUND OF THE INVENTION

1. Field of the Invention

The present invention generally relates to expandable endoprosthesis devices, in particular expandable intraluminal vascular grafts, generally called stents, adapted to be implanted into a body lumen, such as a coronary artery, to maintain the patency of the lumen. These devices are frequently used in the treatment of atherosclerotic stenosis in blood vessels, especially after percutaneous transluminal coronary angioplasty (PTCA) procedures, with the intent to help reduce the likelihood of restenosis of a blood vessel. Stents are also used to support a body lumen where a flap or dissection has occurred or in general where the lumen is weak. The present invention also relates to an expandable intraluminal vascular graft that can be used in any body lumen.

2. Description of Related Art

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guidewire and a dilatation catheter having an inflatable balloon on the distal end thereof are introduced through the guiding catheter with the guidewire slidably disposed within an inner lumen of the dilatation catheter. The guidewire is first advanced out of the distal end of the guiding catheter and is maneuvered into the patient's coronary vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at relatively high pressures (e.g., greater than about 4 atmospheres) and is inflated to a predetermined size (preferably the same as the inner diameter of the artery at that location) to radially compress the atherosclerotic plaque of the lesion against the inside of the artery wall to thereby dilate the lumen of the artery. The balloon is then deflated so that the dilatation catheter can be removed and blood flow resumed through the dilated artery.

By way of example, further details of angioplasty and the devices used in such procedures can be found in U.S. Pat. No. 4,323,071 (Simpson-Robert), U.S. Pat. No. 4,332,254 (Lundquist), U.S. Pat. No. 4,439,185 (Lundquist), U.S. Pat. No. 4,168,224 (Enzmann, et al.), U.S. Pat. No. 4,516,972 (Samson), U.S. Pat. No. 4,582,181 (Samson), U.S. Pat. No. 4,538,622 (Samson, et al.), U.S. Pat. No. 4,597,755 (Samson), U.S. Pat. No. 4,616,652 (Simpson), U.S. Pat. No. 4,748,982 (Horzewski, et al.), U.S. Pat. No. 4,771,778 (Mar), and U.S. Pat. No. 4,793,350 (Mar, et al.), which are hereby incorporated herein in their entirety.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon the deflation of the balloon, a section of the dissected lining (commonly termed a "flap") will collapse into the bloodstream, thereby closing or significantly reducing the blood flow through the vessel. In these instances, surgery is sometimes required to avoid a further blockage of the artery.

Conceivably, the dilatation catheter could be replaced with a perfusion type dilatation catherter such as described in U.S. Pat. No. 4,790,315 (Mueller, Jr. et al.) in order to hold the blood vessel open for extended periods. However, perfusion type dilatation catheters have relatively large profiles which can make advancement thereof through the blockage difficult. Additionally, the inflated balloon of these perfusion catheters can block off a branch artery, thus creating ischemic conditions in the side branch distal to the blockage.

In recent years, various devices and methods (other than bypass surgery) for prevention of restenosis and repairing damaged blood vessels have become known which typically use an expandable cage or region (commonly termed "stent") on the distal end of the catheter designed to hold a detached lining against an arterial wall for extended periods to facilitate the reattachment thereof. Some stents are designed for permanent implantation inside the blood vessel and others are designed for temporary use inside the vessel. By way of example, several stent devices and methods can be found in U.S. Pat. No. 4,998,539 (Delsanti), U.S. Pat. No. 5,002,560 (Machold, et al.), U.S. Pat. No. 5,034,001 (Garrison, et al.), U.S. Pat. No. 5,133,732 (Wiktor), and U.S. Pat. No. 5,180,368 (Garrison).

Typically, the expandable region of these stents is formed by a braided wire attached to the distal end of the catheter body. Such braided designs are often difficult and expensive to manufacture, and can create reliability concerns due to the existence of high stress points located at the connection of the braided wire region with the catheter body and at the connections between the intermingled wire strands.

Alternatively, the expandable stent can be formed by a helical metal or plastic spring that is mechanically restrained in a contracted state during delivery to a predetermined position within a vessel. After placement, the mechanical restraint is released, allowing the helical spring stent to self-expand rapidly against the inner walls of the vessel. Examples of such stents are disclosed in U.S. Pat. No. 4,768,507 (Fischell, et al.), U.S. Pat. No. 4,990,155 (Wilkoff), and U.S. Pat. No. 4,553,545 (Maass, et al.).

In expandable stents that are delivered with expandable catheters, such as balloon catheters, the stents are positioned over the balloon portion of the catheter and expanded from a reduced diameter to an enlarged diameter, greater than or equal to the diameter of the artery wall, by inflating the balloon. Stents of this type can be expanded to an enlarged diameter by deforming the stent, by engagement of the stent walls with respect to one another, and by one-way engagement of the stent walls together with endothelial growth into the stent. Examples of such expandable catheters and stents are disclosed in U.S. Pat. No. 5,102,417 (Palmaz), U.S. Pat. No. 5,123,917 (Lee), and U.S. Pat. No. 5,133,732 (Wiktor) which are hereby incorporated herein in their entirety.

The disadvantage of many of the current expandable stents is that once expanded, they cannot be easily contracted and moved if they are in the wrong position within the lumen. Another problem occurs where the length of the stent shortens when expanded, and the stent is no longer large enough to cover the entire site of repair. In both cases it would be advantageous to be able to contract the stent, withdraw it from the vessel and replace it if necessary, or reposition it before final implantation.

What has been needed, and heretofore unavailable is an intravascular stent that can be placed at the site of a damaged body lumen requiring repair, evaluated, and repositioned if necessary before being locked into place. The present invention fulfills this need.

SUMMARY OF THE INVENTION

The present invention is directed to a stent, adapted to be inserted within a body lumen, and designed to expand and lock in an enlarged diameter form.

The stent of the present invention is designed so that the central portion of the stent body can be reversibly expanded at a selected site within a vessel lumen. Stent deployment can be accomplished by means of a two-stage process which allows the physician to abort the procedure if desired or if a complication develops. In the first stage, the body of the stent is expanded and then evaluated for such criteria as location relative to the stenosis and size relative to the vessel in which it resides. At this stage expansion is reversible and the decision to implant the stent can be aborted. The second stage expands and locks the ends of the stent in place so that the stent remains permanently implanted.

During intravascular surgery, the physician can often only estimate the placement and sizing of the stent when treating a particular lesion. With the present invention, the means for locking the stent into place can be radiopaque. This allows the physician to readily determine the position of the stent relative to the lesion during deployment. The radiopaque ends of the stent allow the stent to be traced without blocking visualization of the lesion, allowing the physician to determine whether the stent is correctly sized to cover the entire lesion. When the physician is satisfied with the stent placement, the ends of the stent are designed to lock the stent in its expanded configuration.

The stent body may be any geometric design that expands in the center when the ends are either twisted or brought closer together. The first and second stages of stent expansion may be accomplished by a number of methods. The stent of the present invention comprises a variety of embodiments. In some embodiments of the stent, the stent is locked in an expanded state by means of a locking ring attached to each end of the stent.

In another embodiment of the stent the locking device comprises a plurality of slots and tabs with teeth such that the slots receive the tabs.

In another embodiment of the stent, the locking device is a ring made from a metal or other suitable material that is capable of undergoing plastic deformation. A material undergoes plastic deformation when the material is subjected to a force greater than its elastic limit, whereby the material stretches irreversibly to an enlarged form. In this embodiment, the locking ring is attached to the individual members of the stent. When the stent is properly positioned at the site of repair in the vessel, the locking end is irreversibly expanded to a larger diameter through plastic deformation of the locking device.

In another embodiment of the stent, the stent and locking device are cut from a flat sheet of a suitable material as a single unit. The locking ends are suitably formed to allow them to irreversibly expand through plastic deformation.

The stent of the present invention may be of a variety of materials, including bio-compatible and bio-resorbable (bio-erodible) polymers, thermal shaped memory polymers or metals, bio-compatible metals, stainless steel, or super elastic materials such as nickel-titanium alloys. A material constituting the stent can be a thin flexible polymer material, such as a polyimide, coated with a thin strengthening material comprising a pyrolytic carbon.

The stent may be deployed in a body lumen through a variety of devices, including but not limited to balloon catheters and specialized stent delivery catheters. These and other advantages of the invention will become more apparent from the following detailed description thereof when taken in conjunction with the accompanying exemplary drawings.

DETAILED DESCRIPTION OF THE INVENTION

It is desirable to provide a stent for repairing vessel walls which has the capability of being flexible when expanded from a reduced to a larger diameter and which can be expanded and contracted in the patient's vessel to ensure proper location and fit. It is also desirable to provide such an expanded stent with a locking mechanism that will lock the stent in its expanded state without sacrificing the flexibility or radial strength of the stent. The present invention achieves these advantages.

Stent deployment can be accomplished by means of a two-stage process which allows the physician to abort the procedure if desired or if a complication develops. In the first stage, the body of the stent is expanded and then evaluated for such criteria as location relative to the stenosis and size relative to the vessel in which it resides. At this stage expansion is reversible and the decision to implant the stent can be aborted. The second stage expands and locks the ends of the stent in place so that the stent remains permanently implanted.

As shown by FIGS. 1–4, the invention is embodied in a stent 1 having an expandable body 5 with locking rings 15 and 25 located at ends 10 and 20 of the stent body.

The stent body is comprised of a plurality of helically shaped elements 32 having ends 35 located at each end of the element. The stent 1 can be formed from a flat sheet of stainless steel or other suitable material, or it can be cut from a section of stainless steel hypotube. When formed from a flat sheet it is rolled to form a cylinder, and may have a plurality of helically shaped cuts 30. The helically shaped cuts extend from the center of the cylinder outward, cutting the cylinder into helically shaped elements 32. The cuts can optionally be formed in such a way that a very small connection is left between the ends 35 of individual helical elements 32, to hold the stent in a contracted, reduced diameter form. These connections are severed when ends 10, 20 are expanded during implantation. The helically shaped elements 32 may also have openings, depicted as holes 31 in FIG. 2 and as slots 33 in FIG. 3, cut into them to reduce weight without sacrificing radial strength or stiffness.

Figure 1:
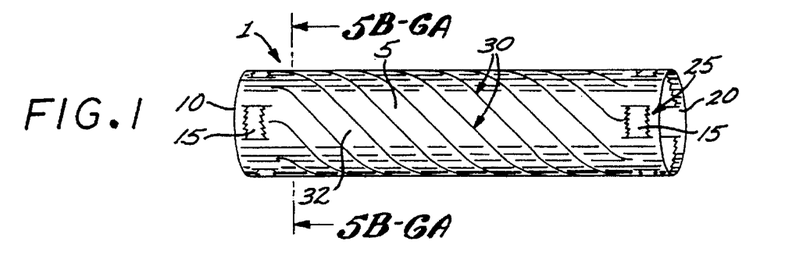
FIG. 1 is a perspective view depicting one embodiment of the present invention.

FIG. 1 depicts an embodiment of stent 1 in a contracted state having a reduced diameter. In this state the outer diameter of the stent is substantially the same over its entire length, including the two locking ends 10 and 20. This reduced diameter state allows the stent to be slidably engaged on the distal end of a suitable catheter, and introduced into a patient's vasculature.

Figure 2:
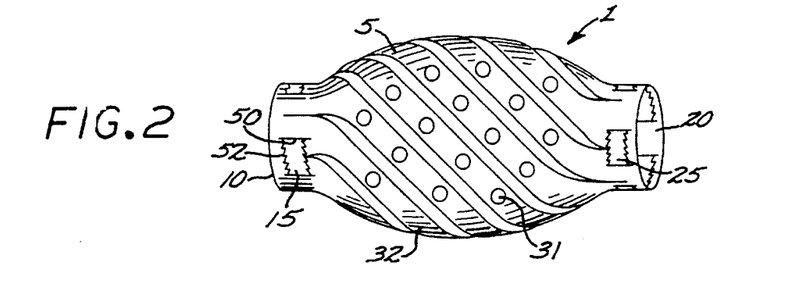
FIG. 2 is a perspective view of the stent of FIG. 1 depicting the stent body in an expanded state, and the ends in their original contracted state.

FIG. 2 depicts the stent in an intermediate state where the body 5 of the stent 1 has an enlarged diameter, but the locking ends 10, 20 of the stent remain in a contracted, reduced diameter. This intermediate state is achieved, due to the construction of the helical elements 32 of the expandable body 5, by either twisting the ends of stent 1 in a counter rotating manner relative to each other, or by twisting and at the same time reducing the overall length of the stent by reducing the longitudinal distance between ends 10 and 20. Further illustration of this process is presented below.

Figure 4A:
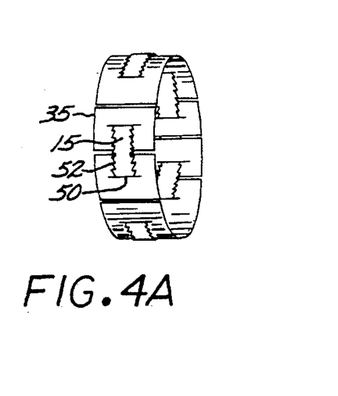
FIG. 4A is a perspective view depicting the locking ring mechanism of one embodiment of the invention in a contracted state.

FIG. 4A is a perspective view of a locking end representative of locking ends 10, 20. The helically shaped elements 32 of the expandable body 5 have ends 35 with slots 50 adapted to receive a locking ring 15. The locking ring has a plurality of teeth 52 either along both its first and second edges, or only along one edge. These teeth 52 are formed to engage the edges of slot 50 in such a way that the teeth 52 may slide through slot 50 in only one direction. This allows the locking end to expand to a second enlarged diameter state, but prevents contraction to a reduced diameter state.

Figure 3:
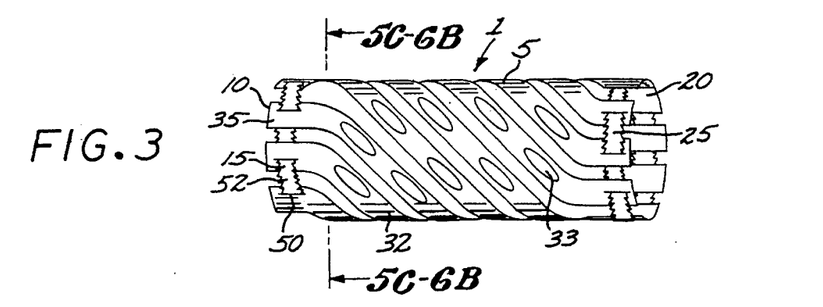
FIG. 3 is a perspective view of the stent of FIGS. 1 and 2 depicting the stent in a fully expanded form with the ends locked in place.
Figure 4B:
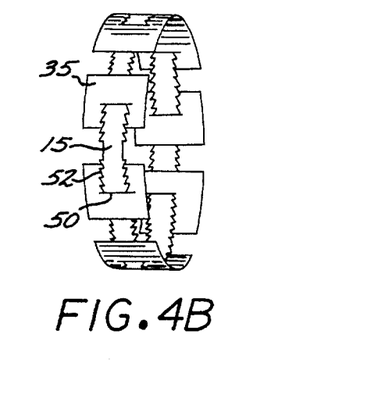
FIG. 4B is a perspective view of the locking ring depicted in a locked state.
Figure 5A:
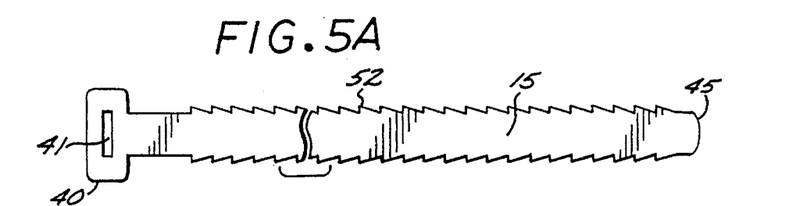
FIG. 5A is a plan view of the locking ring depicted in an unrolled state.

FIG. 3 depicts the stent 1 in a final enlarged state. In this view, both the expandable body 5 and the locking ends 10, 20 have expanded larger diameters suitable for fixing the stent in position within a vessel. FIG. 4B is a perspective view of locking end 10 illustrating how the ends 35 of the helical elements 32 of the expandable body 5 move apart as the end 10 expands, and how teeth 52 on locking ring 15 engage the edges of slot 50 to lock the end 10 in an enlarged diameter. FIG. 5C, a cross-sectional view taken along the line 6—6 of FIG. 3, further illustrates the interaction between helical element ends 35, locking ring 15 and locking ring end 40.

FIGS. 5A–C and 6A–B depict the structure of the locking end in more detail. Locking ring 15 has a first end portion 40 having a slot or a loop 41. The second end 45 of locking ring 15 is threaded through the ends 35 of the helically shaped elements 32 of the expandable body 5 and then through the slot 41 in locking ring end 40. Locking ring 15 is suitably long so that it is retained within the slot 41 of locking ring end 40 when the stent end 10 is fully enlarged during implantation, as shown in FIG. 5C. The teeth 52 on the edges of locking ring 15 allow the slots 50 in the ends 35 of the helical elements 32 to slide along the locking ring as the stent end 10 of stent 1 expands, but do not allow them to return to their original position, thus locking the ends 10, 20 of the stent in an enlarged diameter state.

Figure 5B:
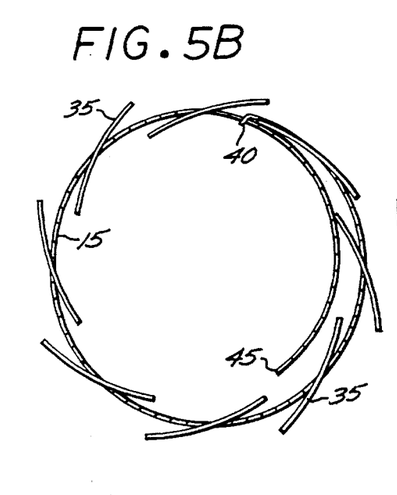
FIG. 5B is a cross-sectional view taken along line 5—5 depicting the stent in a rolled and reduced diameter form with the free end of the locking ring shown tucked inside of the stent.
Figure 5C:
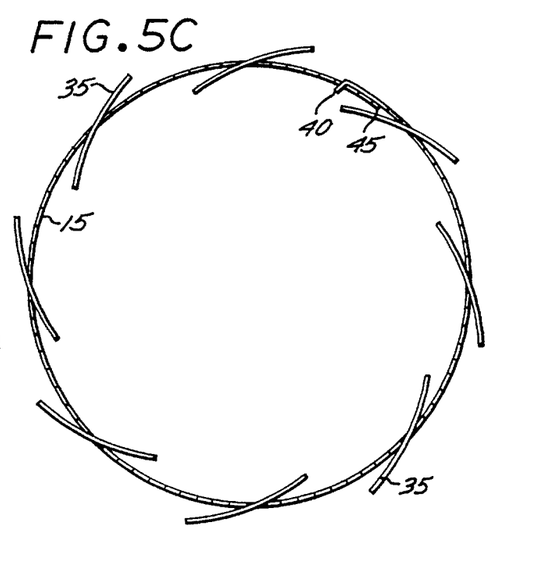
FIG. 5C is a cross-sectional view taken along line 6—6 depicting the stent in an unrolled and expanded diameter form with the free end of the locking ring shown tucked inside of the stent.
Figure 6A:
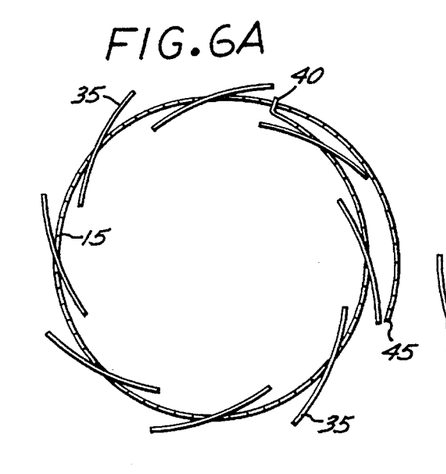
FIG. 6A is a cross-sectional view taken along line 5—5 depicting an alternative embodiment of the stent in a rolled and reduced diameter form with the free end of the locking ring shown overlapping the exterior of the stent.
Figure 6B:
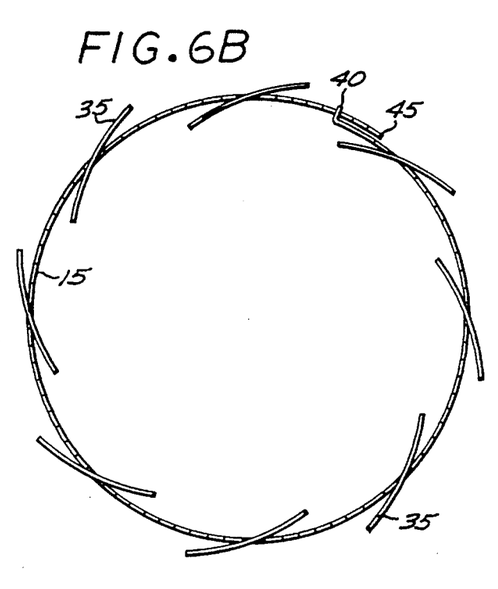
FIG. 6B is a cross-sectional view taken along line 6—6 depicting an alternative embodiment of the stent in an unrolled and expanded diameter form with the free end of the locking ring shown overlapping the exterior of the stent.

FIGS. 5B–C depict locking ring 15 with locking ring end 45 threaded towards the interior of the stent. Locking ring 15 may also be threaded through expandable element ends 35 in the alternate manner depicted in FIG 6A, with locking ring end 45 overlapping the exterior of the stent. Either alternative is equally suitable in the present invention.

Figure 7A:
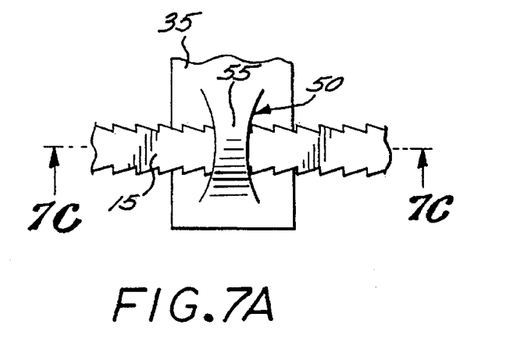
FIG. 7A is a plan view depicting one method of attaching the locking ring of the present invention to the body of the stent.
Figure 7B:
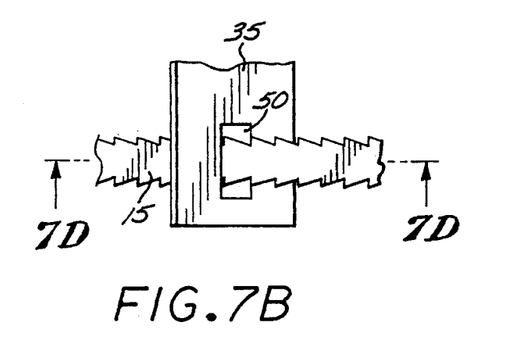
FIG. 7B is a plan view depicting another method of 15 attaching the locking ring of the present invention.
Figure 7C:
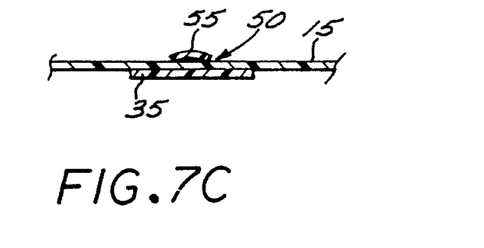
FIG. 7C is a partial cross-sectional view taken along line 7C—7C depicting a portion of the locking ring of the present invention where it is attached to the body of the stent.
Figure 7D:
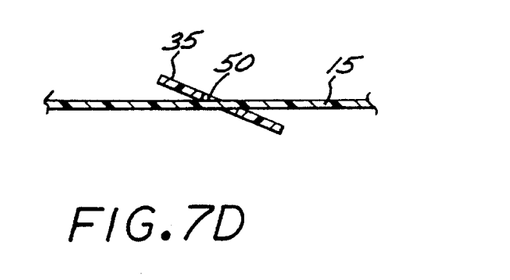
FIG. 7D is a partial cross-sectional view taken along line 7D—7D depicting a portion of the locking ring where it engages the body of the stent.

Several locking mechanisms can be employed to securely fix the locking ends in an expanded and locked configuration. As shown in FIGS. 7A and 7C, locking ring 15 extends through a pair of slots 50 which are formed in ends 35. The bridge 55 is slightly raised or curced to allow locking ring 15 to pass through slots 50. Teeth 52 engage the slots 50 as the locking ring 15 is expanded. As can be seen in FIG. 7A, teeth 52 point in one direction so that after locking ring 15 is expanded the teeth engage the slots 50 and prevent locking ring 15 from collapsing or recoiling. Another embodiment for locking ring 15 in its expanded configuration is shown in FIGS. 7B and 7D. The method of locking is the same as that described for FIGS. 7A and 7C.

Figure 8:
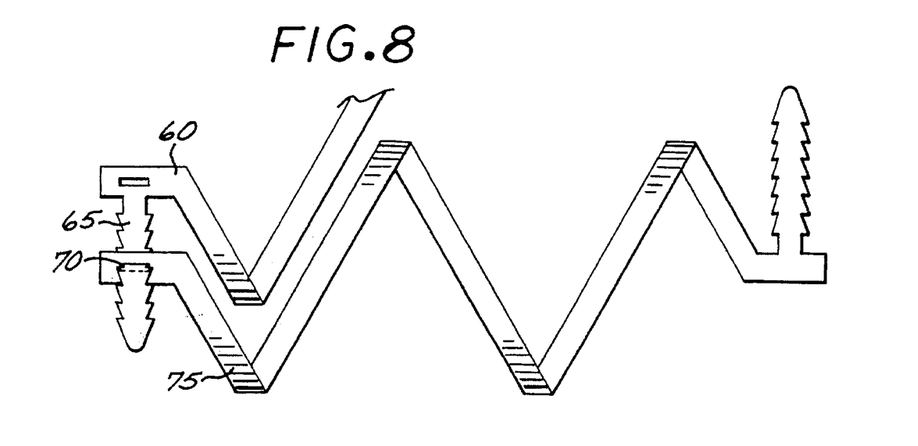
FIG. 8 depicts an embodiment of the present invention having individual helical shaped members comprising the body of the stent, and using a system of tabs and slots at each end of the member to form the locking device.

FIG. 8 is another embodiment of the present invention. Stent 1 can be formed from a plurality of helically shaped members 60, each having at least one end having a toothed tab 65 projecting perpendicular to the longitudinal axis of member 60, and a slot 70.

In a first, contracted state, helically shaped members 60 are arranged to form a substantially cylindrical stent. In this arrangement, toothed tabs 65 are threaded through slot 70, in such a fashion that adjacent tabs 65 overlap each other. The tabs remain overlapping in a contracted state during expansion of the body of the stent. When the stent has been positioned within a vessel lumen, the ends of the stent are then expanded by any suitable means, such as inflating an inflatable balloon on the distal end of a dilating catheter, such as shown in FIG. 9C, causing a reduced overlap of tab 65 at each end of each member 60 of the stent. As inflatable balloon 210 continues to expand, the toothed portions of tab 65 interact with slot 70 to engage in a locking manner, and, once engaged, to stay engaged with a high degree of reliability.

Figure 10:
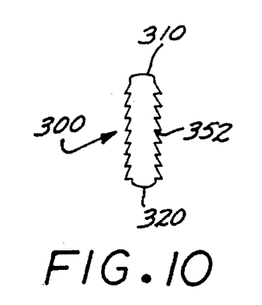
FIG. 10 is a plan view of another embodiment of the locking device depicted in an unrolled state.
Figure 11:
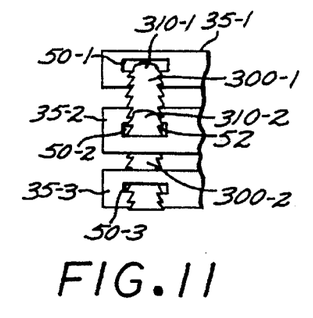
FIG. 11 is a plan view depicting one method of attaching the locking ring of FIG. 10 to the body of the stent.
Figure 11A:
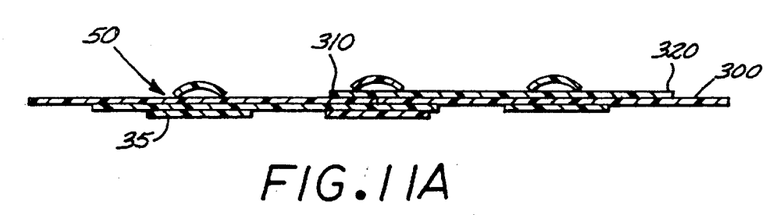
Figure 11B:
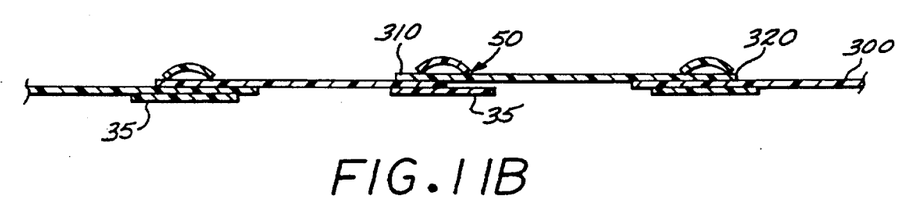

An alternative embodiment of the locking ring is depicted in FIG. 10. Locking member 300 is substantially shorter than the embodiment of the locking ring shown in FIG. 5A. Locking member 300 is designed to span the distance between two adjacent helically shaped element ends 35. As depicted in FIG. 11, a plurality of locking members 300 are used to connect helically shaped elements ends 35 to construct the stent in rolled form. FIG. 11 illustrates how locking member 300 is used to interconnect ends 35 of the helically shaped elements 32 to form the stent. A plurality of helically shaped members 32 are arranged so that locking member 300 can be slid through the slots 50 in the ends 35 of two adjacent helically shaped members 32. As shown in FIG. 11A, locking member ends 310 and 320 overlap other locking members 300 when the stent is in a reduced diameter form. When the locking end is expanded, as depicted in FIG. 11B, the overlap of individual locking members 300 is substantially reduced. Each locking member has teeth 352 situated on at least one of its longitudinal edges that are designed to engage the edges of slot 50, thus irreversibly locking the ends of the stent in an enlarged diameter form. It will be obvious to one skilled in the art that other embodiments of a locking device can be incorporated into an intravascular stent that will allow the stent to be used during the two-stage implantation process described herein. Any combination of locking device and reversibly expandable stent body construction that allows the body of the stent to be first expanded and then, in a second step, irreversibly locked into place will be within the scope of this invention.

Figure 12A:
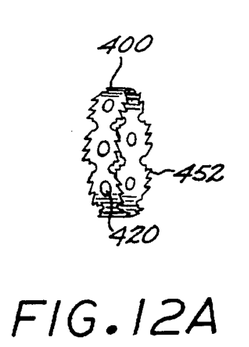
FIG. 12A is a perspective view of another embodiment of the locking ring depicted in a reduced diameter state.
Figure 12B:
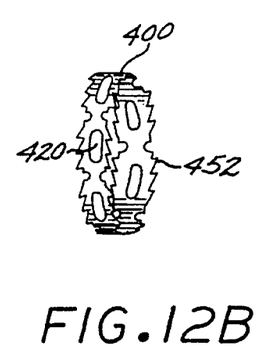
FIG. 12B is a perspective view of the locking ring of FIG. 12A in an expanded diameter form.
Figure 13A:
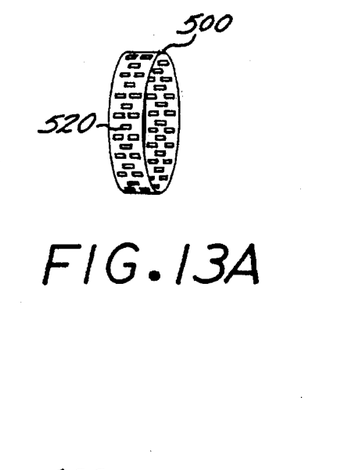
FIG. 13A is a plan view depicting an embodiment of the locking ring in a reduced diameter form.
Figure 13B:
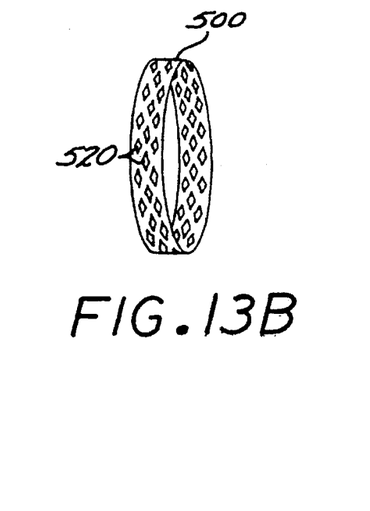
FIG. 13B is a perspective view depicting the embodiment of the locking ring of FIG. 13A in an expanded diameter form.
Figure 14A:
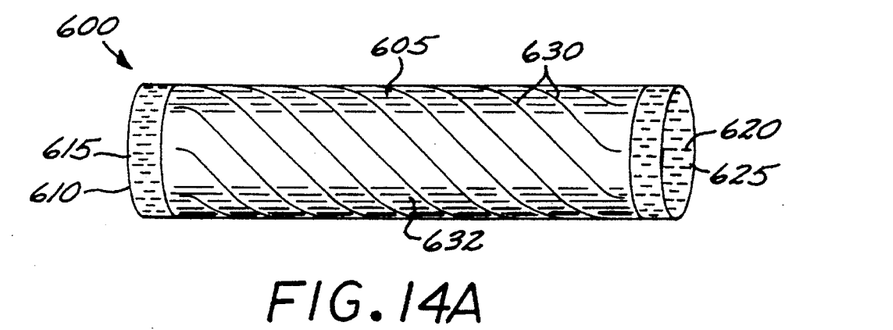
FIG. 14A is a perspective view of an embodiment of the stent and locking rings depicting the stent in its original, reduced diameter form.
Figure 14B:
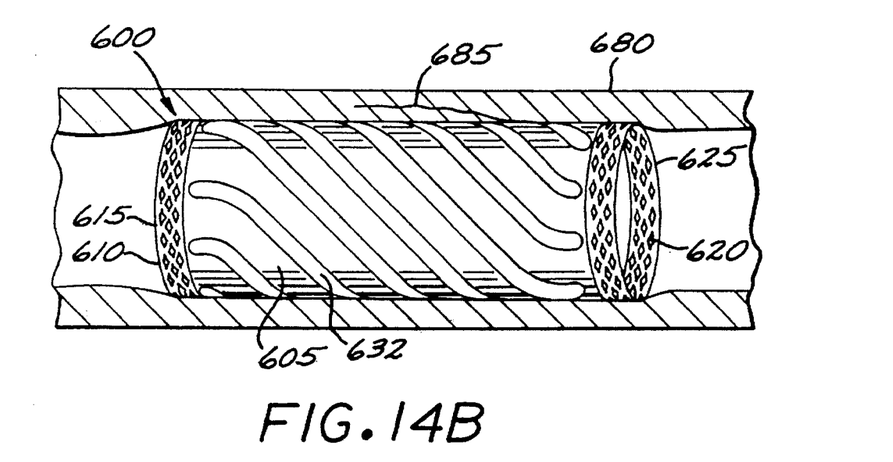
FIG. 14B is a perspective view of the stent of FIG. 14A in a fully expanded form with the ends locked in place depicted within the lumen of a vessel.

Examples of other potential embodiments of the present invention are described in FIGS. 12–14. The previous embodiments have shown the locking device as an expandable device that expands by way of the locking ring end or member moving in relation to the ends 35 of the stent. It is possible, however, to construct the locking device from a material that undergoes irreversible plastic deformation when it expands. Such an embodiment of the locking device is disclosed in FIGS. 12A and 12B. In FIG. 12A, locking ring 400 is depicted in a contracted, reduced diameter form. Locking ring 400 is depicted having teeth 452 as discussed previously to engage slots 50 located on ends 35 of helical elements 32. Locking ring 400 also has openings 420, which can be any shape, for example round holes, slots, or ovals. The addition of holes 420 and their location on the locking device 400 allows the device to irreversibly plastically deform when a force greater than the elastic limit of the material is applied to expand the locking device. FIG. 12B illustrates the locking ring 400 of FIG. 12A in an expanded larger diameter form. Locking device 400 is shown having cut outs 425 on both edges that allow the width of the locking device to reduce as it is enlarged.

FIG. 13A shows a locking ring 500 similar to that shown in FIG. 12A except that the openings are depicted as slots 520 and there are no teeth on the edges. FIG. 13B depicts the stent of FIG. 13A in expanded diameter form.

Although previous embodiments have shown locking devices such as that depicted in FIG. 5A as threading through slots on the ends of the helically shaped members 32, it is possible to construct a stent such as that shown in FIG. 14A by attaching the locking rings to the ends of the stent. Stent 600 is shown in a rolled reduced diameter form having helically shaped elements 632 comprising an expandable body 605. The helically shaped elements 632 are separated by slots or slits 630. Attached to each end are locking devices 610 and 620. FIG. 14B depicts the stent of FIG. 14A in its expanded enlarged diameter form within the lumen of a vessel 680 compressing a flap 685 against the vessel wall.

Figure 15A:
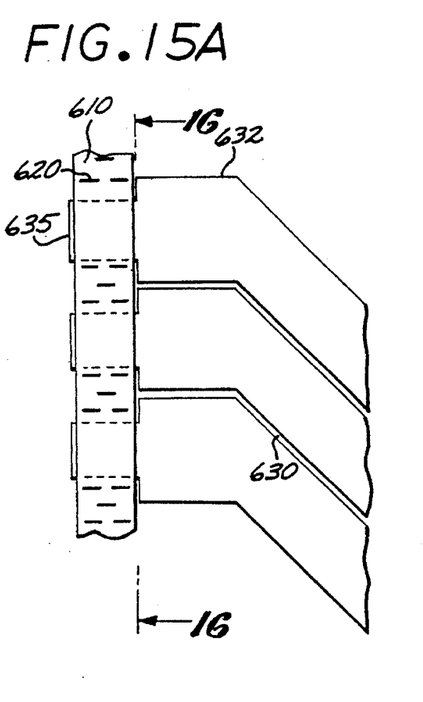
FIG. 15A is an enlarged plan view depicting a portion of the locking end assembly of the stent of FIG. 14A.
Figure 15B:
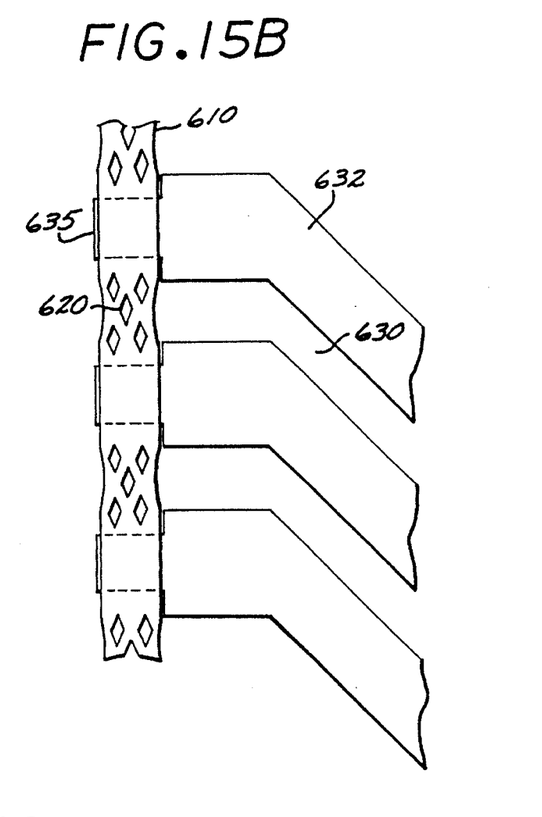
FIG. 15B is a partial enlarged plan view of the locking end of the stent of FIG. 14B depicted in an enlarged diameter form.
Figure 16:
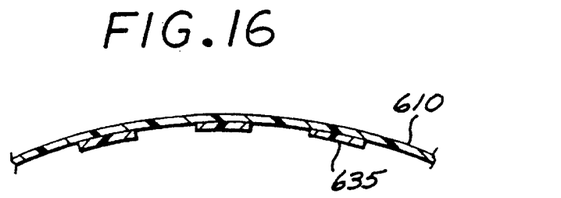
FIG. 16 is a partial cross-sectional view taken along the line 15—15 depicting an embodiment showing the attachment of the locking ring to the interior of the stent body.
Figure 17:
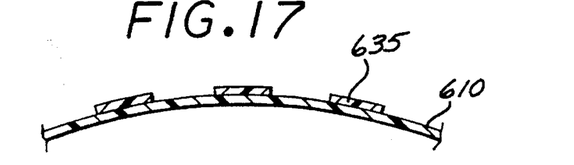
FIG. 17 is a partial cross-sectional view taken along the line 15—15 depicting an alternative orientation and attachment of the locking ring to the exterior of the stent body.

Locking devices 610 and 600 can be attached to the ends of stent body 605 in a variety of ways. FIGS. 15A and 15B depict one embodiment of such an attachment method. In this embodiment, individual helical elements 632 having tabs 635 on each end are attached to locking device 610 using a suitable adhesive, bio-compatible solder, spot welding, or other suitable attachment means. FIG. 15B depicts the device of FIG. 15A in an expanded enlarged diameter form. Tabs 635 can be attached to locking device 610 on either the internal surface as depicted in FIG. 16, or on the external surface of locking ring 610 as depicted in FIG. 17. Either attachment means is suitable since expansion of the locking device 610 is independent of the placement or method of attachment of the tabs 635.

Figure 18A:
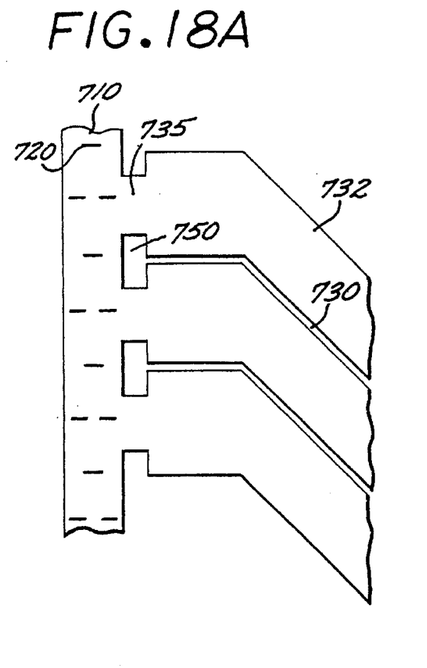
FIG. 18A is an enlarged partial plan view depicting an alternative embodiment where the locking end and the stent expandable body are manufactured as a single piece in a reduced diameter form.
Figure 18B:
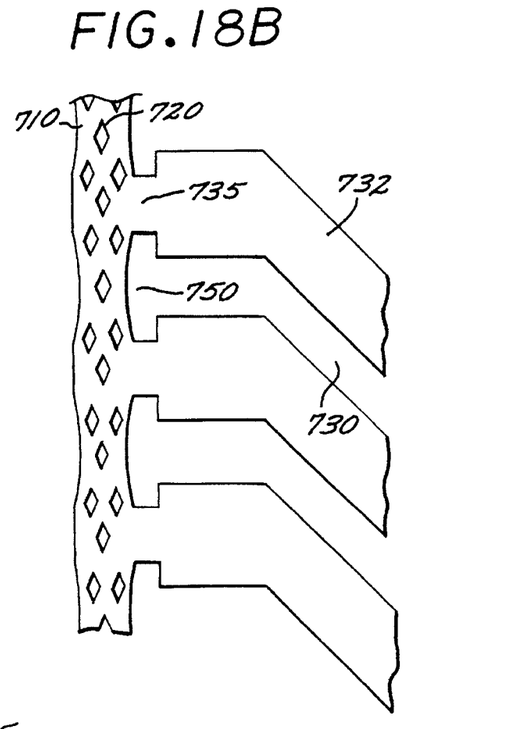
FIG. 18B is an enlarged partial plan view depicting the stent of FIG. 18A in an enlarged diameter form.

FIGS. 18A and 18B illustrate another embodiment of the invention wherein the locking devices and the helically shaped elements 732 are fabricated from a single piece or sheet of an appropriate material that is capable of irreversible plastic deformation. The stent 700 can be fabricated from a single sheet with an appropriate metal, using a computer controlled laser or waterjet cutter. The laser or waterjet cutter is used to cut openings 720, notches 750 and slots 730. Once the complex shape of the locking device 710 and the expandable body 705 has been cut from the sheet of material, the sheet is rolled into a cylindrical form and the longitudinal edges of the sheet are joined using a suitable attachment method. The attachment method can be adhesive, solder, spot welding, brazing, or any other metal joining method suitable for joining the edges of an intravascular stent. Construction of a stent in this manner is particularly beneficial in that it allows high quality, reliable, and low cost manufacturing of the stent.

Figure 19A:
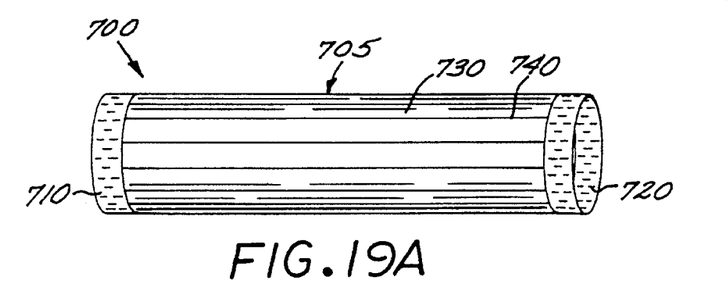
FIG. 19A is a perspective view of an embodiment of the stent and locking rings, depicted in a reduced diameter form, wherein the elements of the expandable body are linearly shaped.
Figure 19B:
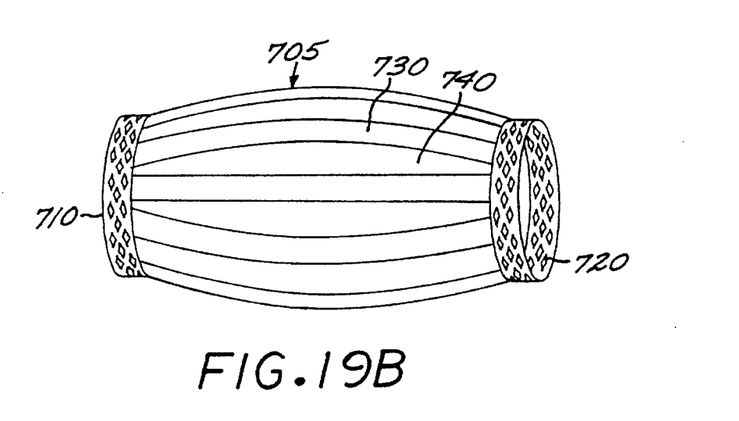
FIG. 19B is a perspective view depicting the stent and locking rings of FIG. 19B in an enlarged diameter form.

FIGS. 19A and 19B illustrate another embodiment of the invention wherein the individual elements 730 that comprise the expandable body 705 of stent 700 are linear in shape and are separated from each other by slots or cuts 740. Expansion of expandable body 705, as depicted in FIG. 19B, causes the linearly shaped elements 730 to bow radially outwardly and contact the vessel wall. Expansion of locking ends 710, 720 is similar to other embodiments of the invention previously described.

In another embodiment of the invention as depicted at FIGS. 20A–D, stent 1, in its contracted reduced diameter state, is mounted on the distal end of catheter 800 with locking ends 10,20 slidably engaging proximal balloon 840 and distal balloon 845 respectively. A steerable dilatation catheter 800 having a pair of tubular members coaxially arranged is provided in order to implant stent 1. Dilatation catheter 800 has an outer member 810 and an inner member 815 which are coaxially arranged and can be moved axially with respect to one another. Dilatation balloon 840 is mounted on outer member 810 and distal balloon 845 is mounted on inner member 815. The outer member is attached at its proximal end to knob 811 which can be rotated and in turn rotates outer member 810 and proximal balloon 840. Likewise, inner member 815 is attached at its proximal end to knob 816 and when the knob is rotated it imparts rotational movement to inner member 815 and distal balloon 845. Further, knob 816 can be moved axially with respect to knob 811 thereby creating axial displacement between the balloons.

Figure 20A:
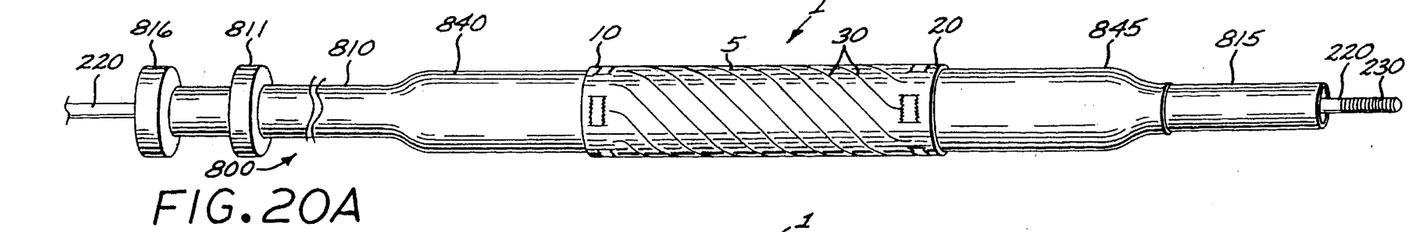
FIG. 20A is a planned view depicting an embodiment of the invention in a contracted form mounted on a pair of inflatable balloons in tandem arrangement wherein the distal portion of the locking ring is mounted on the distal balloon and the proximal locking ring is mounted on the proximal balloon.
Figure 20B:
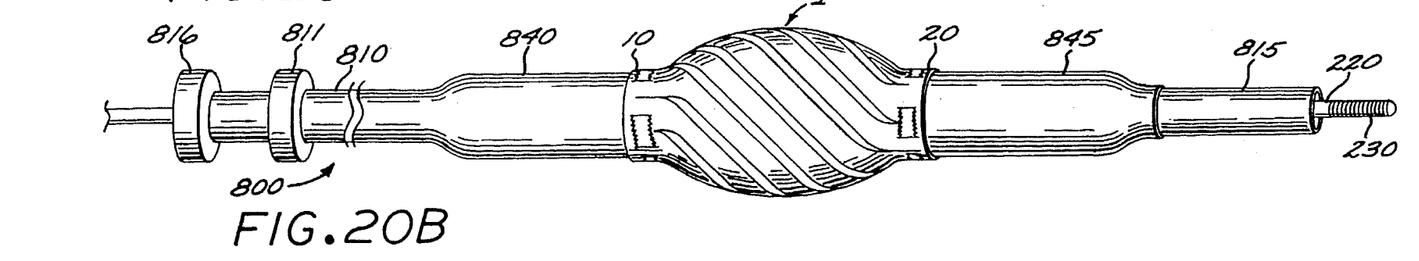
FIG. 20B is a plan view depicting the stent and catheter wherein the stent body has been expanded.
Figures 20C, 20D:
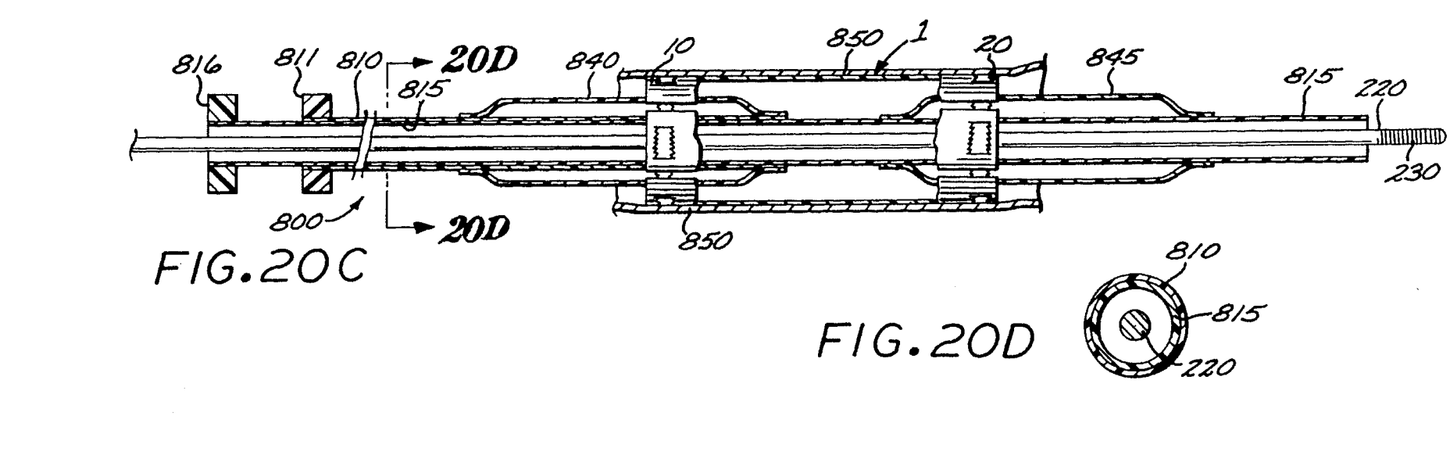
FIG. 20C is a plan view of the stent and dilatation catheter of FIG. 20A depicting the stent partially cut away to show the two dilatation balloons expanding the locking rings on the stent.
FIG. 20D is a cross-sectional view taken along line 20D—20D depicting the coaxial arrangement of the outer member and the inner member each of which carries one of the dilatation balloons.

Referring more specifically to FIG. 20B, knobs 811 and 816 have been counterrotated and knob 816 withdrawn proximally so as to impart rotational movement to stent 1 and to simultaneously shorten the distance between locking ends 10,20. Thus the body of stent 1 is expanded while locking ends 10,20 remain in engagement with proximal balloon 840 and distal balloon 845 respectively. As can be seen in FIG. 9C, proximal balloon 840 and distal balloon 845 have been inflated, thereby expanding locking ends 10 and 20 to their fully expanded and locked positions. Thereafter, the balloons are deflated and the catheter assembly is withdrawn from the vasculature or body lumen 850 leaving the expanded stent implanted at the body lumen 850. FIG. 20D depicts the coaxial arrangement of outer member 810 and inner member 815 with guidewire 220 passing through the inner member.

Figure 9A:
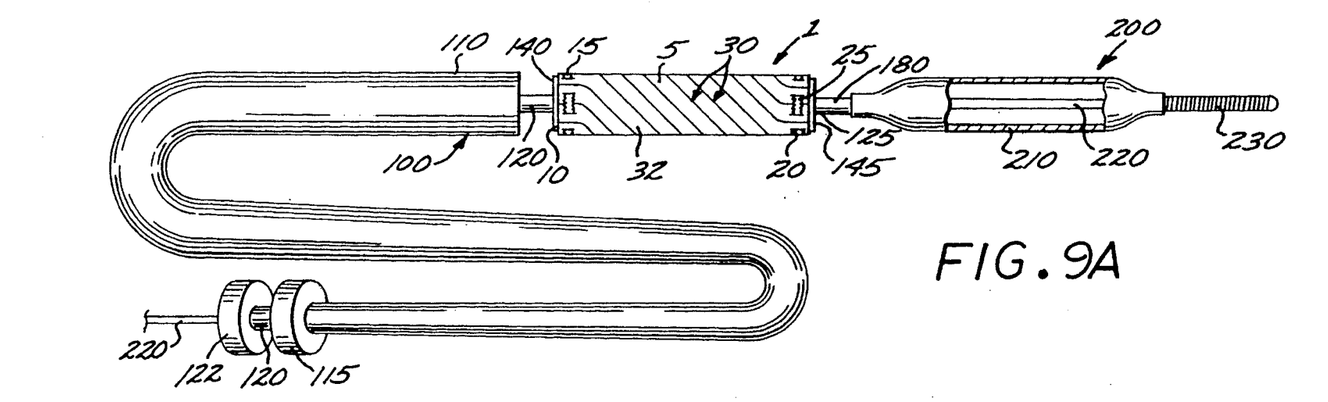
FIG. 9A is a plan view depicting a version of the invention in a contracted form mounted on a catheter coaxially arranged with a steerable dilatation catheter.
Figure 9B:
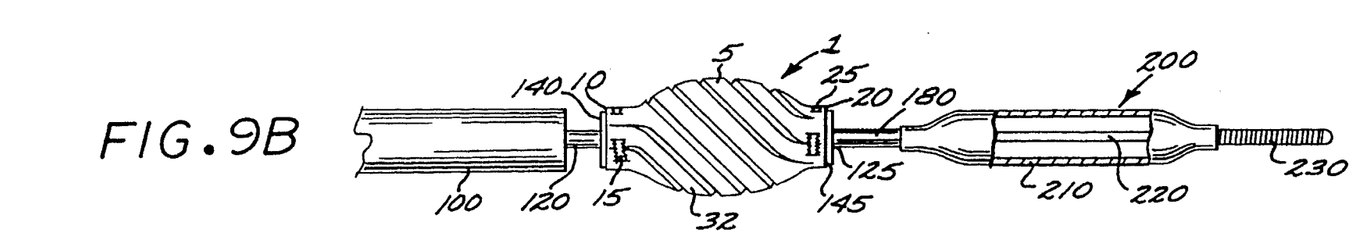
FIG. 9B is a plan view depicting the stent and catheter in an expanded form.
Figure 9C:
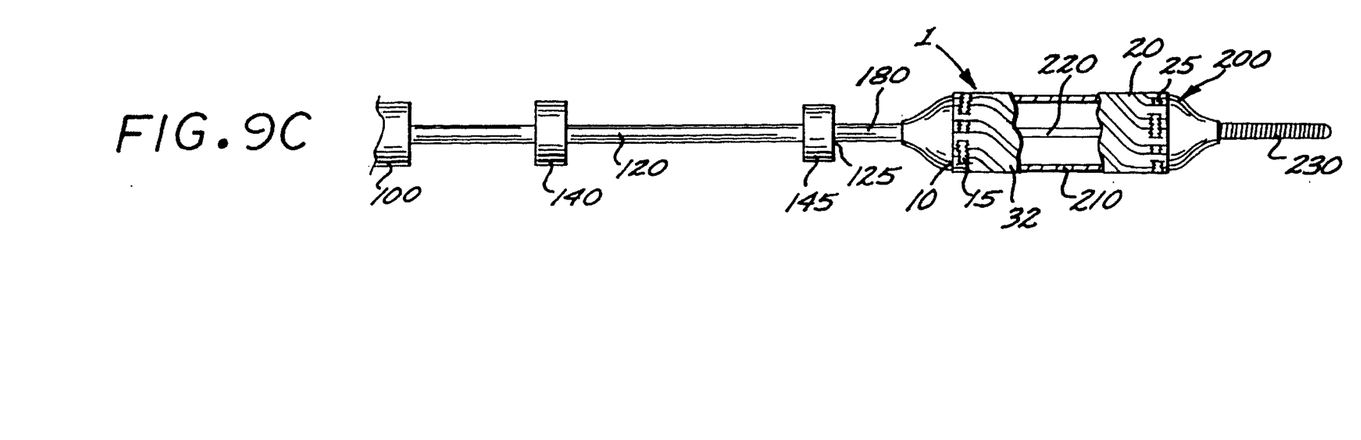
FIG. 9C is a plan view of the stent and dilatation catheter of FIG. 9A depicting the stent, partially cut away to show the dilatation balloon, in an enlarged state whereby the ends of the stent are locked in an enlarged form.

Referring to FIGS. 9A–C for example purposes, the operation of the stent of the present invention will be described. As shown in FIG. 9A, the stent 1, in its contracted reduced diameter state, is mounted on the distal end of a catheter 100 with locking ends 10, 20 slidably engaging collars 140, 145 respectively. A steerable dilatation catheter 200 having a dilatation balloon 210 mounted on a tubular member 180, co-axially arranged on a core member 220, and terminating with a helical coil 230 is percutaneously introduced into a vessel and tracked by fluoroscope until the location of the vascular lesion to be treated is reached. The catheter 100 is then mounted on the steerable dilatation catheter 200 by threading tubular member 180 through the central lumen 125 of the catheter 100. The catheter 100 is then slidably moved along tubular member 180, its progress tracked by fluoroscope, until the stent 1 is positioned at the site to be repaired.

To facilitate visualization of stent 1 at the repair site, one or both of the locking rings 15 at the ends 10, 20 may be radiopaque. The radiopaque material can be gold, platinum-iridium, or any other commonly known material visible under fluoroscopy. It should be apparent that rendering only the rings 15, located at the ends 10, 20 of the stent 1, is advantageous because the rings can be used as markers to define the area where the stent will contact the vessel wall without obscuring the repair site. This allows the physician to ensure proper positioning of the stent.

Collar 140, depicted here separated from catheter body 110 for clarity, is, in actuality attached to catheter body 110. Collar 145 is mounted on an inner tubular member 120, co-axially arranged within catheter body 110 and having a central lumen 125. Both inner tubular member 120 and central lumen 125 extend to the proximal end of catheter body 110.

Using an embodiment shown in FIG. 9A as an example, when the stent 1 is properly positioned, the physician rotates and pulls knob 122 mounted on the proximal end of inner tubular member 120 in a proximal direction. Collar 140 remains essentially stationary while collar 145 is pulled axially in a proximal direction by inner tubular member 120. As the axial distance between collar 140 and 145 decreases, force is applied to locking ends 10, 20 and acts to radially expand and reduce the length of stent 1. Due to the shape of the helical elements 32 of expandable body 5, the forces expand the stent body 5 radially outwardly into contact with the vessel wall, and reduces its length. This expansion causes the central portion of expandable body 5 to expand radially outwardly and contact the vessel walls, but leaves locking ends 10,20 still engaged on collars 140,145 in a contracted, reduced diameter state. With a stent as shown in FIGS. 19A and 19B, which has non-helical slits, there is no need to counterrotate the locking ends as the body of the stent is expanded by axial movement. This is not the case when the stent is helically shaped.

When stent 1 is formed of helically shaped elements 32, reducing the axial length of stent 1 while simultaneously rotating the locking 10,20, either individually or together, results in the stent expanding radially outwardly into contact with the vessel wall. Collars 140, 145 may be attached to the catheter body 110 or inner tubular member 120 respectively in such a manner that the collar turns freely as the axial length of the stent 1 is shortened. Preferably, the collars are firmly attached to their respective catheter members. This allows the physician to rotate knob 122 as he pulls knob 122 in a proximal direction, thus assisting the expansion of stent 1.

As will be apparent from FIGS. 19A–B, rotation of locking ends 710, 720 does not occur when stent 700 is formed of linearly shaped elements 730.

While knob 122 is depicted in FIG. 9A as the means for rotating inner tubular member 120, it will be apparent that any means capable of grasping the inner tubular member 120 or catheter body 110 and applying torque to the catheter body 110 or inner tubular member 120 can be used.

Alternatively, catheter 100 may be constructed so that inner tubular member 120 is rotated causing collar 145 to rotate while collar 140 remains fixed. When the inner tubular member is rotated in an appropriate direction, the rotation causes the expandable body 5 to expand, but leaves locking ends 10, 20 in a first reduced diameter state.

A principle advantage of the present invention is that once the stent expandable body 5 has been expanded, the physician can check the positioning and sizing of the stent 1 in relation to the vascular defect to be repaired. If stent size or positioning is not adequate to repair the defect, the stent may be contracted to a reduced diameter and either withdrawn from the vessel, or repositioned before final expansion and implantation. All other implantable prior art stents undergo irreversible expansion during implantation. Thus, the present invention is a major step forward in the repair of vascular defects.

Contraction of expandable body 5 of stent 1 to a reduced diameter state is accomplished in essentially the reverse order of expansion. By pushing inner tubular member 120 in a distal direction and simultaneously rotating one or both locking ends 10,20, collar 145 will move in a distal direction relative to collar 140. This causes locking end 20, slidably engaged on collar 145, to move in a distal direction. Since locking end 10 is engaged to collar 140 which is attached to the catheter body 110, the distal motion of collar 145 and rotation of locking end 20 results in an increase of the axial length of stent 1, thus causing the expandable body 5 to contract radially inwardly and return to a contracted, reduced diameter state. Once this reduced diameter state is attained, the stent 1 and catheter 100 may be either withdrawn from the vessel or repositioned.

When the physician is satisfied with the sizing and placement of stent 1 in the vessel, final implantation is accomplished as follows. Catheter 100 is slowly withdrawn in a proximal direction, releasing locking ends 10, 20 of stent 1 from collars 140, 145 respectively. It should be noted that while locking ends 10, 20 engage collars 140, 145 with sufficient force to remain engaged during the expansion of expandable body 5 to an enlarged diameter, contact with the vessel wall is sufficient to retain the stent in position and overcome the engaging force when catheter 100 is slowly withdrawn.

When catheter 100 has been withdrawn leaving stent 1 in position, the steerable dilatation catheter 200 is moved proximally until the expandable portion of the dilatation balloon 210 is positioned within the length of stent 1. The dilatation balloon is then expanded by forcing a noncompressible fluid through tubular member 180. The expansion of balloon 210 causes locking ends 10, 20 to expand to an enlarged diameter state, as shown in FIG. 9C. The teeth 52 of locking ring 15 irreversibly engage the edges of slots 50 of edges 35 and slot 40 of locking ring 15 to lock the stent 1 in an enlarged diameter state, thereby holding the vessel open. The dilatation balloon is then deflated, and the steerable dilation catheter is withdrawn from the vessel leaving stent 1 implanted.

Any embodiment of the stent may be formed from a variety of materials, including bio-compatible and bio-resorbable polymers, thermal shape memory polymers or metals, bio-compatible metals, stainless steel, or super elastic materials, such as nickel-titanium alloys. A material constituting the stent can be a thin flexible polymer material, such as a polyimide, coated with a thin strengthening material comprising a pyrolytic carbon. Furthermore, in all of the embodiments of stents disclosed herein, the material comprising the stent may be made of a bio-degradable material, and may be a material impregnated with a drug, so the stent may locally treat a particular lesion or disease.

Expansion of stent 1 from a reduced diameter form into an expanded diameter form may be performed by any means that can expand the central body of the stent either by twisting the ends while simultaneously shortening the longitudinal length of the stent, and then subsequently expanding the ends of the stent and locking rings into a final enlarged diameter form. Furthermore, the present stent is not limited to use in coronary arteries and over-the-wire angioplasty catheter systems; the stent may also be deployed in any body lumen by any suitable means such as use of a so-called rapid exchange catheter system.

The stent of the present invention as described in all of the foregoing embodiments may be used not only in cardiovascular procedures, but also in urinary, prostate, renal, cerebral, nasal, auditory, rectal, aortic and other medical procedures.

Furthermore, it should be understood that any dimensions associated with the above described embodiments are not intended to limit the invention to only those dimensions. For example, while certain dimensions might be appropriate for a stent used in a coronary artery, these same dimensions might not be suitable for a stent used in other areas of a patient's vasculature or other body lumen. It is also understood that the drawings are not necessarily to scale.

Other modifications can be made to the present invention by those skilled in the art without departing from the scope thereof. While several particular forms of the invention have been illustrated and described, it will also be apparent that various modifications can be made without departing from the spirit and scope of the invention.

I claim:

1. An intraluminal stent implantable in a body lumen, comprising:

a cylindrical stent body having a first reduced diameter and an adjustable second expanded diameter;

a first end and a second end on said cylindrical stent body;

means for expanding said cylindrical stent body from said first reduced diameter to said adjustable second expanded diameter so that said cylindrical stent body engages said body lumen;

means for expanding said first end and said second end from a first reduced diameter to an adjustable, second expanded diameter, so that said first end and said second end lock said cylindrical stent body in an expanded configuration;

means for locking said first end and said second end in said second expanded diameter;

said locking means including at least one ring having at least a pair of overlapping edges; and a plurality of teeth on at least one of said overlapping edges;

whereby said rings are expanded from said first diameter to said adjustable, second expanded diameter so that said teeth engage in an interlocking relationship to hold said rings in said second expanded diameter configuration.

2. The intraluminal stent of claim 1, wherein said overlapping edges have at least one slot and at least one tab, said tab extending through said slot to form said interlocking relationship.

3. The intraluminal stent of claim 2, wherein said tab contains said teeth.

4. The intraluminal stent of claim 1, wherein said teeth in said slot are connected to adjacent teeth transverse to said teeth in said slot.

5. The intraluminal stent of claim 1, wherein at least one said ring is radiopaque.

6. An intraluminal stent implantable in a body lumen, comprising:

a cylindrical body portion formed of a sheet having longitudinally extending edges, further having a first end and a second end perpendicular to the longitudinal edges;

a plurality of slots on said first end and second end of said sheet;

a pair of locking rings, each having:
at least a pair of overlapping edges; and
a plurality of teeth on at least one of said overlapping edges;

whereby said rings are expanded from a first diameter to an adjustable, second expanded diameter so that said teeth engage in an interlocking relationship to hold said rings in said adjustable, second expanded diameter form;

whereby said slots receive said rings.

7. The intraluminal stent of claim 6, wherein one of said overlapping edges in said ring has at least one slot, the other said overlapping edge has at least one tab, said tab engaging said slot to form said interlocking relationship.

8. The intraluminal stent of claim 7, wherein said slot contains said teeth.

9. The intraluminal stent of claim 8, wherein said teeth in said slot are connected to adjacent teeth transverse to said teeth in said slot.

10. The intraluminal stent of claim 7, wherein said tab contains said teeth.

11. The intraluminal stent of claim 10, wherein said tabs are threaded through said slots on said end perpendicular to said longitudinal edge of said sheet.

12. The intraluminal stent of claim 11, whereby said rings are expanded from a first diameter to an adjustable, second expanded diameter so that said teeth on said tabs engage said slots in said first end and said second end perpendicular to said longitudinal edge of said sheet in an interlocking relationship to hold said cylindrical body in said adjustable second expanded diameter.

13. The intraluminal stent of claim 6, wherein at least one said ring is radiopaque.

14. The intraluminal stent of claim 6, further comprising a means for retaining said cylindrical body portion in said first reduced diameter form until it is expanded to said adjustable second expanded diameter form.

15. The intraluminal stent of claim 14, wherein said means for retaining said cylindrical body portion in said first diameter position comprises a plurality of break-away tabs along both edges perpendicular to said longitudinal edges.

16. The intraluminal stent of claim 6, wherein said cylindrical body portion has a plurality of helical cuts to enable expansion of said cylindrical body.

17. The intraluminal stent of claim 16, wherein said cylindrical body portion has a plurality of apertures for increasing the flexibility of the stent.

18. The intraluminal stent of claim 17, wherein said apertures are in the form of a plurality of elongated apertures transversely aligned with said cylindrical body.

19. The intraluminal stent of claim 18, wherein said elongated apertures alternate with said helical cuts.

20. An intraluminal stent implantable in a body lumen, comprising:

a cylindrical body formed from a plurality of strips disposed along a longitudinal direction; each of said strips having a first end and a second end perpendicular to the longitudinal edges of said strip; said stent further having a tab and a slot for receiving said tab located at the first end and the second end, said body and said ends further having a first reduced diameter and an adjustable second expanded diameter; and said plurality of said strips, arranged adjacent to one another, interconnected at said first end and said second end to one another to form said cylindrical body.

21. The intraluminal stent of claim 20, wherein said tabs contain teeth.

22. The intraluminal stent of claim 20, wherein said slots receive said tabs, said tabs overlapping with said tabs from said adjacent strips, to form said cylindrical body.

23. The intraluminal stent of claim 20, whereby said ends of said cylindrical body are expanded from said first reduced diameter to said adjustable, second expanded diameter so that said teeth on said tabs located on said strips engage said slots in an interlocking relationship to hold said ends of said strips in said adjustable second expanded diameter form.

24. The intraluminal stent of claim 20, wherein said strips are formed in a helical configuration.

25. A method for repairing a patient's vasculature or other body lumen having an occluded or partially occluded portion, comprising:

mounting a cylindrical stent body on a catheter, said cylindrical stent body having a first reduced diameter and an adjustable, expanded second diameter;

advancing said catheter in said patient's vasculature to position said stent body across the site of repair;

expanding said body of said stent at said site of repair;

checking said expanded second diameter and placement of said stent in relation to said site of repair by using flouroscopy;

contracting said stent body to said first, reduced diameter form; and withdrawing said catheter and stent from the vasculature or other body lumen.

26. The method of claim 25, wherein said method steps for expanding, checking and contracting said cylindrical stent body comprises twisting in a counter-rotating manner a first end and a second end of said stent body.

27. The method of claim 28, wherein said method steps for expanding, checking, and contracting said cylindrical stent body comprises decreasing the length of said stent.

* * * * *

UNITED STATES PATENT AND TRADEMARK OFFICE
CERTIFICATE OF CORRECTION

PATENT NO. : 5,556,413
DATED : September 17, 1996
INVENTOR(S) : Sharon Lam

It is certified that error appears in the above-indentified patent and that said Letters Patent is hereby corrected as shown below:

Column 14, Claim 27, Line 63, change "claim 28", to read --claim 25--.

Signed and Sealed this

Twentieth Day of May, 1997

*Attest:*

BRUCE LEHMAN

*Attesting Officer*

*Commissioner of Patents and Trademarks*